(12) United States Patent
Koka

(10) Patent No.: US 7,872,120 B2
(45) Date of Patent: Jan. 18, 2011

(54) METHODS FOR SYNTHESIZING A COLLECTION OF PARTIALLY IDENTICAL POLYNUCLEOTIDES

(76) Inventor: Venkata Chalapathi Rao Koka, 3210 Merryfield Row, San Diego, CA (US) 92121

( * ) Notice: Subject to any disclaimer, the term of this patent is extended or adjusted under 35 U.S.C. 154(b) by 308 days.

(21) Appl. No.: 11/836,868

(22) Filed: Aug. 10, 2007

(65) Prior Publication Data

US 2009/0043086 A1  Feb. 12, 2009

(51) Int. Cl.
*C07H 21/00* (2006.01)
(52) U.S. Cl. ............... 536/25.3; 536/25.31; 536/25.32; 536/25.33; 536/25.34
(58) Field of Classification Search ............ None
See application file for complete search history.

(56) References Cited

U.S. PATENT DOCUMENTS

| 6,521,427 | B1 | 2/2003 | Evans |
| 6,738,502 | B1 | 5/2004 | Coleman et al. |
| 2005/0181387 | A1* | 8/2005 | Messier ............... 435/6 |
| 2007/0054277 | A1 | 3/2007 | Evans |

OTHER PUBLICATIONS

Patten et al. Curent Opinion in Biotechnology (1997), vol. 8, pp. 724-733.*
Eaton et al. Bioorganic & Medicinal Chemistry (1997), vol. 5, pp. 1087-1096.*
Kumar, et al., "MEGA3: Integrated software for Molecular Evolutionary Genetics Analysis and sequence alignment," Briefings in Bioinformatics, 5(2): 150-163 (2004).
PCT International Search Report dated Sep. 11, 2008.

\* cited by examiner

*Primary Examiner*—Patrick T Lewis
(74) *Attorney, Agent, or Firm*—Kirk Baumeister

(57) ABSTRACT

Methods for synthesizing a collection of partially identical polynucleotides are disclosed.

4 Claims, 6 Drawing Sheets

Figure 2

```
Collection Polynucleotide 1 (SEQ ID NO: 1)  ATGAGACAGACTTTGCCTTGTATCTACTTTTGGGGGCCTTTTGCCCTTTGGGATGCTG
Collection Polynucleotide 2 (SEQ ID NO: 2)  ATGAGACAGACTTTGCCTTGTATCTACTTTTGGGGGCCTTTTGCCCTTTGGGATGCTG
Collection Polynucleotide 3 (SEQ ID NO: 3)  ATGAGACAGACTTTGCCTTGTATCTACTTTTGGGGGCCTTTTGCCCTTTGGGATGCTG
                                                                                   113
                                                              74
Collection Polynucleotide 1 (SEQ ID NO: 1)  TGTGCATCCTCCAGCACCAAGTGCACTGTTAGCCATGAAGTTGCTGACTGCAGCCACCTG
Collection Polynucleotide 2 (SEQ ID NO: 2)  TGTGCATCCTCCAGCACCAAGTGCACTGTTAGCCATGAAGTTGCTGACTGCAGCCACCTG
Collection Polynucleotide 3 (SEQ ID NO: 3)  TGTGCATCCTCCAGCACCAAGTGCACTGTTAGCCATGAAGTTGCTGACTGCAGCCACCTG
                                                      128
Collection Polynucleotide 1 (SEQ ID NO: 1)  AAGTTGACTCAGGTACCCGATGAT 144
Collection Polynucleotide 2 (SEQ ID NO: 2)  AAGTTGACTCAGGTACCCGATGAT 144
Collection Polynucleotide 3 (SEQ ID NO: 3)  AAGTTGAGTCAGGTACCCGATGAT 144
```

Collection Polynucleotide 1
(SEQ ID NO: 1; 144 nt or 144 bp depending on synthesis method)

US 7,872,120 B2

```
                            SEQUENCE LISTING

<160> NUMBER OF SEQ ID NOS: 9

<210> SEQ ID NO 1
<211> LENGTH: 144
<212> TYPE: DNA
<213> ORGANISM: Homo sapiens

<400> SEQUENCE: 1
atgagacaga ctttgccttg tatctacttt tgggggggcc ttttgccctt tgggatgctg      60
tgtgcatcct ccagcaccaa gtgcactgtt agccatgaag ttgctgactg cagccacctg     120
aagttgactc aggtacccga tgat                                            144

<210> SEQ ID NO 2
<211> LENGTH: 144
<212> TYPE: DNA
<213> ORGANISM: Artificial Sequence
<220> FEATURE:
<223> OTHER INFORMATION: A human derived TLR3 receptor variant
      containing a c to g mutation at residue 74 and a g to c
      mutation at residue 113.

<400> SEQUENCE: 2
atgagacaga ctttgccttg tatctacttt tgggggggcc ttttgccctt tgggatgctg      60
tgtgcatcct ccagcaccaa gtgcactgtt agccatgaag ttgctgactg cacccacctg     120
aagttgactc aggtacccga tgat                                            144

<210> SEQ ID NO 3
<211> LENGTH: 144
<212> TYPE: DNA
<213> ORGANISM: Artificial Sequence
<220> FEATURE:
<223> OTHER INFORMATION: A human derived TLR3 receptor variant
      containing a c to g mutation at residue 128.

<400> SEQUENCE: 3
atgagacaga ctttgccttg tatctacttt tgggggggcc ttttgccctt tgggatgctg      60
tgtgcatcct ccaccaccaa gtgcactgtt agccatgaag ttgctgactg cagccacctg     120
aagttgagtc aggtacccga tgat                                            144

<210> SEQ ID NO 4
<211> LENGTH: 48
<212> TYPE: DNA
<213> ORGANISM: Artificial Sequence
<220> FEATURE:
<223> OTHER INFORMATION: DNA encoding amino acid residues 1-16 of
      human TLR3.

<400> SEQUENCE: 4
atgagacaga ctttgccttg tatctacttt tgggggggcc ttttgccc                   48

<210> SEQ ID NO 5
<211> LENGTH: 48
<212> TYPE: DNA
<213> ORGANISM: Artificial Sequence
<220> FEATURE:
<223> OTHER INFORMATION: DNA encoding amino acid residues 17-32 of
``` human TLR3 variant containing a c to g mutation.

<400> SEQUENCE: 5
tttgggatgc tgtgtgcatc ctccagcacc aagtgcactg ttagccat                48

<210> SEQ ID NO 6
<211> LENGTH: 48
<212> TYPE: DNA
<213> ORGANISM: Artificial Sequence
<220> FEATURE:
<223> OTHER INFORMATION: DNA encoding amino acid residues 17-32 of
      human TLR3.

<400> SEQUENCE: 6
tttgggatgc tgtgtgcatc ctccaccacc aagtgcactg ttagccat                48

<210> SEQ ID NO 7
<211> LENGTH: 48
<212> TYPE: DNA
<213> ORGANISM: Artificial Sequence
<220> FEATURE:
<223> OTHER INFORMATION: DNA encoding amino acid residues 33-48 of
      human TLR3.

<400> SEQUENCE: 7
gaagttgctg actgcagcca cctgaagttg agtcaggtac ccgatgat                48

<210> SEQ ID NO 8
<211> LENGTH: 48
<212> TYPE: DNA
<213> ORGANISM: Artificial Sequence
<220> FEATURE:
<223> OTHER INFORMATION: DNA encoding amino acid residues 33-48 of
      human TLR3 variant containing a g to c mutation.

<400> SEQUENCE: 8
gaagttgctg actgcaccca cctgaagttg actcaggtac ccgatgat                48

<210> SEQ ID NO 9
<211> LENGTH: 48
<212> TYPE: DNA
<213> ORGANISM: Artificial Sequence
<220> FEATURE:
<223> OTHER INFORMATION: DNA encoding amino acid residues 33-48 of
      human TLR3 variant containing a c to g mutation.

<400> SEQUENCE: 9
gaagttgctg actgcagcca cctgaagttg agtcaggtac ccgatgat                48

METHODS FOR SYNTHESIZING A COLLECTION OF PARTIALLY IDENTICAL POLYNUCLEOTIDES

FIELD OF THE INVENTION

The present invention relates to methods for synthesizing a collection of partially identical polynucleotides.

BACKGROUND OF THE INVENTION

Modern polynucleotide synthesis techniques are utilized in high-throughput automated processes capable of generating large numbers of individual polynucleotide sequences at relatively high yields. The size of the polynucleotide sequences made using such methods may range from small primer-sized polynucleotides containing well below 50 nucleotides to massive gene, plasmid or chromosome-sized polynucleotides containing more than $1\times10^{10}$ nucleotides. The high yields attained by most modern polynucleotide synthesis techniques are, in part, the result of synthesis methods that join many smaller polynucleotide sequences to create a larger individual polynucleotide sequence.

Importantly, libraries comprising very large numbers of polynucleotides with unique sequences encoding variant versions of a given recombinantly expressed protein can be synthesized using these methods. Such libraries are particularly desirable when developing protein-based therapeutics such as monoclonal antibodies and other recombinant proteins. This is because the variant proteins encoded by the individual polynucleotides in the library can later be screened for properties, such as improved in vivo half-life or binding affinity, that are sought in therapeutic proteins.

Typically, such libraries are known in the art as "fully combinatorial" libraries. This means that if two different nucleotide residues present in a parent sequence are to be changed relative to the parent sequence, all possible combinations of the two changed positions will be represented by the sequences of the individual polynucleotides in the library (FIG. 1). Stated differently, the number of unique variant sequences represented by such a library would be described by the product of the binomial coefficients for each position in the sequence to be varied minus one (one is subtracted from the product since the parent sequence cannot be considered a variant, but is one possible combination which would result). For example, in a "fully combinatorial" library where only two nucleotides residues are to be varied (e.g by mutation of positions 74 and 128 to G residues) relative to the parent sequence the number of unique variant sequences (V) in the library would be described by the following equation:

$$V = [(C(n,k)_{varied\ position\ 1}) * (C(n,k)_{varied\ position\ 2})] - 1$$

where the binomial coefficient for varied position 1 is $$(C(n,k)_{varied\ position\ 1}) = n! / [k!(n-k)!]$$

where n is the number of possible unique nucleotide residues at the position and k is the number of positions where the residues can be placed and $$(C(n,k)_{varied\ position\ 2}) = n! / [k!(n-k)!]$$

Here, $(C(n,k)_{varied\ position\ 1}) = n!/[k!(n-k)!] = 2!/[1!(2-1)!] = 2$ and $C(n,k)_{varied\ position\ 2}) = n!/[k!(n-k)!] = 2!/[1!(2-1)!] = 2$ so $V = [(2)(2)] - 1 = 3$.

The number of unique variants produced in this simple "fully combinatorial" library example is also easily seen to be 3 upon examination of FIG. 1.

One problem with "fully combinatorial libraries" is that this approach to library construction and synthesis is not compatible with rational mutagenesis strategies. In rational mutagenesis only individual polynucleotides containing specifically varied positions that have been rationally designed are sought-not all possible combinations of these varied positions. Synthesis of all possible combinations of variations when all that is sought is a collection of rationally designed unique, partially identical individual polynucleotide sequences inefficiently uses synthesis reagents and time.

Thus, a need exists for methods that facilitate the high throughput synthesis of a collection of unique, partially identical individual polynucleotide sequences.

BRIEF DESCRIPTION OF THE DRAWINGS

FIG. 2 shows a multiple sequence alignment of variants of wild-type Homo sapiens Toll-like Receptor 3 (TLR3) molecules. Mutations relative to the wild-type Homo sapiens TLR3 sequence at each varied position are shown in bold and underlined in Collection Polynucleotide 1 (SEQ ID NO: 1), Collection Polynucleotide 2 (SEQ ID NO: 2), and Collection Polynucleotide 3 (SEQ ID NO: 3).

SUMMARY OF THE INVENTION

Figure 1:
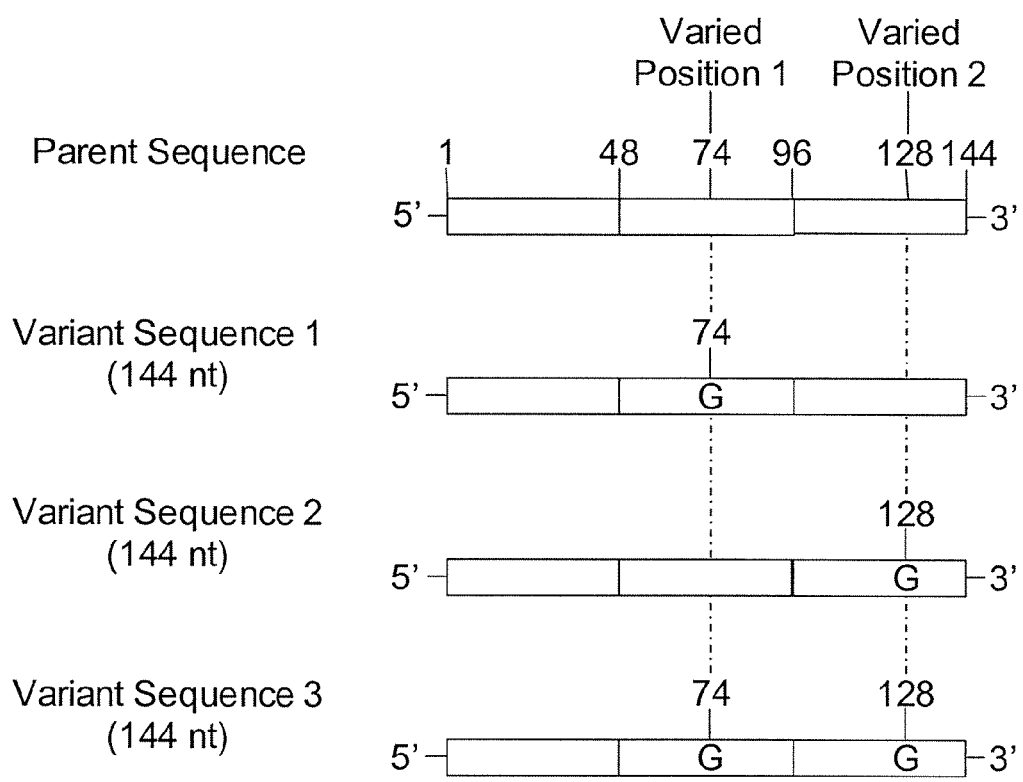
FIG. 1 shows the number of unique variant polynucleotide sequences in a simple example of a fully combinatorial library. Mutations placing a G residue at positions 74 and 128 are shown.

One aspect of the invention is a method for synthesizing a collection of partially identical polynucleotides comprising identifying a collection of unique, partially identical individual polynucleotide sequences to be synthesized; analyzing the polynucleotide sequences with a phylogeny tree algorithm to make a phylogenetic tree; identifying each individual branch group of the phylogenetic tree; identifying each individual polynucleotide sequence in each individual branch group identified; dividing each individual polynucleotide sequence in each branch group into smaller polynucleotide sequences; identifying the smaller polynucleotide sequences common to all the individual polynucleotide sequences in each individual branch group identified if the branch group contains more than one individual polynucleotide sequence; comparing the smaller polynucleotide sequences common to all the individual polynucleotide sequences in a first branch group with the smaller polynucleotide sequences from all other branch groups; identifying the smaller polynucleotide sequences common to all branch groups; identifying the smaller polynucleotide sequences common to only a subset of branch groups; identifying the smaller polynucleotide sequences unique to each individual polynucleotide sequence in each branch group; providing the smaller polynucleotide sequences of the preceding three steps required to synthesize an individual polynucleotide sequence in a branch group; synthesizing the individual partially identical polynucleotide sequence; and repeating the preceding two steps until each individual polynucleotide sequence in the collection of partially identical polynucleotides is synthesized.

DETAILED DESCRIPTION OF THE INVENTION

All publications, including but not limited to patents and patent applications, cited in this specification are herein incorporated by reference as though fully set forth.

The term "partially identical" as used herein means that at least one nucleic acid residue in a first sequence is identical to the nucleic acid residue at the corresponding position in a second sequence when a collection of sequences is aligned using a multiple sequence alignment algorithm.

The CLUSTAL algorithm is an example of a multiple sequence alignment algorithm. Typically, the CLUSTALW algorithm is used with the default settings of the program implementing the algorithm, but user defined settings may be used. Multiple sequence alignments can also be performed using the CLUSTALX or T-COFFEE algorithms. Those skilled in the art will recognize other appropriate multiple sequence alignment algorithms and settings for use with such algorithms.

The term "phylogenetic tree" as used herein means a cladogram that graphically represents the relatedness of a collection of polynucleotide sequences relative to each other or the equivalent data that when graphically plotted describes the relatedness of a collection of polynucleotide sequences relative to each other.

Phylogenetic trees useful in the methods of the invention can be generated using algorithms that calculate the evolutionary distance between the members of a collection of unique, partially identical individual polynucleotide sequences or which utilize a measure of nucleotide substitutions, such as evolutionary distance, in conjunction with other criteria to generate a cladogram. Such phylogenetic trees may be rooted or unrooted. Tests of phylogeny such as the Bootstrap test, or Interior Branch test may also be applied to the determination of phylogenetic trees useful in the methods of the invention. See Kumar et al., *Brief Bioinform.* 5, 150 (2004).

Evolutionary distances represent the relatedness of sequences by measuring the number of nucleotide substitutions occurring between them. If the evolutionary distance between two sequences is larger, then the sequences have more substitutions relative to each other. Such sequences can be considered to be more dissimilar. If the evolutionary distance between two sequences is small, then the sequences have fewer substitutions relative to each other. Such sequences can be considered to be more similar.

The term "subset of branch groups" means a branch or set of branches that does not include all individual branches identified on a phylogenetic tree. At a minimum, a "subset of branch groups" on a phylogenetic tree may contain a single branch group comprising more than one individual polynucleotide sequence. In other more complex collections of individual polynucleotides this "subset" may include more than one branch group, but such a subset could not include all branch groups identified on a phylogenetic tree for such a collection.

One aspect of the invention is a method for synthesizing a collection of partially identical polynucleotides comprising identifying a collection of unique, partially identical individual polynucleotide sequences to be synthesized; analyzing the polynucleotide sequences with a phylogeny tree algorithm to make a phylogenetic tree; identifying each individual branch group of the phylogenetic tree; identifying each individual polynucleotide sequence in each individual branch group identified; dividing each individual polynucleotide sequence in each branch group into smaller polynucleotide sequences; identifying the smaller polynucleotide sequences common to all the individual polynucleotide sequences in each individual branch group identified if the branch group contains more than one individual polynucleotide sequence; comparing the smaller polynucleotide sequences common to all the individual polynucleotide sequences in a first branch group with the smaller polynucleotide sequences from all other branch groups; identifying the smaller polynucleotide sequences common to all branch groups; identifying the smaller polynucleotide sequences common to only a subset of branch groups; identifying the smaller polynucleotide sequences unique to each individual polynucleotide sequence in each branch group; providing the smaller polynucleotide sequences of the preceding three steps required to synthesize an individual polynucleotide sequence in a branch group; synthesizing the individual partially identical polynucleotide sequence; and performing the preceding two steps until each individual polynucleotide sequence in the collection of partially identical polynucleotides is synthesized.

In the methods of the invention a collection of unique, partially identical individual polynucleotide sequences to be synthesized is identified. Typically, such a collection of partially identical individual polynucleotides comprises a series of unique variants of a parent polynucleotide sequence. The individual sequences included in such a collection may be, for example, a parent polynucleotide sequence encoding a peptide chain and a number of variant polynucleotide sequences that contain nucleotide changes relative to the parent sequence. These nucleotide sequence changes can produce desired amino acid changes in the peptide chains encoded by these variant polynucleotides. Alternatively, the polynucleotide sequences may simply be a collection of partially identical polynucleotide sequences that encode homologs of a peptide chain from different animal species, polynucleotide sequences that encode different isoforms of a peptide chain expressed by a single animal species, or polynucleotide sequences that encode different members of a family of peptide chains.

Such nucleotide sequences may be rationally designed or picked at random. Variations in the polynucleotide sequences may also be created to reduce the likelihood of hybridization of a given polynucleotide with a second polynucleotide molecule, or hybridization occurring within a given polynucleotide sequence that produces a secondary structures such as "stem-loop" type structures. Variations in a polynucleotide sequence may also be desirable to eliminate sites of protein interaction with a given polynucleotide sequence. Such sites may be restriction sites or transcription factor binding sites. In some instances it may also be desirable to introduce variations into a polynucleotide sequence, such as a ribozyme or other catalytically active nucleotide sequence, that alter the activity of such molecules. Those skilled in the art will recognize other types of polynucleotide sequence variation (e.g. wobbly bases) and motivations for creating variations in a collection of polynucleotide sequences.

In the methods of the invention the unique, partially identical individual polynucleotide sequences to be synthesized are analyzed with a phylogeny tree algorithm to make a phylogenetic tree. A typical phylogenetic tree useful in the methods of the invention is a graphical representation of the phylogeny tree algorithm calculated evolutionary distances between each individual polynucleotide sequence, or "leaf", on the "tree" or the equivalent data describing such a graphical display. The evolutionary distance between two individual polynucleotide sequences on such a tree is represented by the total distance measured from the first species through the nearest branch points or root on the tree and then to the second species on the tree. Stated differently, the evolutionary distance between two individual polynucleotide sequences on a phylogenetic tree is represented by the length of the shortest line connecting the two sequences that can be traced on the tree.

In the methods of the invention the data submitted for analysis by the phylogeny tree algorithm is typically the output data from a multiple sequence alignment algorithm analysis that has been applied to the collection of unique, partially identical individual polynucleotide sequences to be synthesized. Such algorithms are discussed above. In some instances, additional data describing the polynucleotide sequences in the collection or the relationship of these sequences to each other can be utilized by the phylogeny tree algorithm.

In the methods of the invention the phylogeny tree algorithm can use the Neighbor-Joining method and the default settings for this method in the Mega3.1 Molecular Evolutionary Genetics Analysis Program (see Kumar et al., supra) to calculate the evolutionary distances between each individual polynucleotide sequence in the collection of unique, partially identical polynucleotides to be synthesized. These settings include the use of the Kimura 2-Parameter Model for calculating evolutionary distances.

The phylogeny tree algorithm useful in the methods of the invention may also utilize the Minimum Evolution (ME), Maximum Parsimony (MP), or Unweighted Pair Group Method with Arithmetic mean (UPGMA) or other similar techniques to determine the relatedness of collections of polynucleotide sequences (Kumar et al., supra). Standard settings for these methods are well known and will be recognized by those of ordinary skill in the art. Such settings may include, for example, the use of the number of differences between sequences, the p-distance between sequences, the Jukes-Cantor model, the Tajima-Nei model, the Tamura 3-Parameter model, the Tamura-Nei model, the Log-Det method, or the Syn-Nonsynonymous methods for calculating evolutionary distances (Kumar et al., supra).

In the methods of the invention each individual branch group of the phylogenetic tree is identified. A branch group is identified by examining a phylogenetic tree—or the underlying data represented by such a tree—to spot the nodes on the tree, such as a root or branch point, and then determining which polynucleotide sequences are connected to a given node on the tree by shorter evolutionary distances relative to other more distant sequences.

A branch group does not include all individual polynucleotide sequences found on a phylogenetic tree. For example, the simplest phylogenetic tree that might be constructed would describe the relationship between just two individual polynucleotide sequences. Such a simple phylogenetic tree would have two branch groups that each contain a single polynucleotide sequence. However, a more complex phylogenetic tree would describe the relatedness of a large collection of individual polynucleotides. Such a phylogenetic tree would have a complex topology and branch groups containing more than one individual polynucleotide could be readily identified on such a tree by one of ordinary skill in the art.

In the methods of the invention each individual polynucleotide sequence in each individual branch group is identified. This step is performed by determining which individual polynucleotide sequences on the phylogenetic tree are present in each branch group identified on the tree.

In the methods of the invention each individual polynucleotide sequence in each branch group is divided into smaller polynucleotide sequences. Typically, this division is accomplished conceptually using the sequence data describing an individual polynucleotide sequence. Such division may involve symmetrically dividing the sequence, when possible, or asymmetrically dividing the sequence. Asymmetrical division may be desirable in instances where a smaller polynucleotide sequence is already physically available as a synthesis reagent and can be identified within a larger individual polynucleotide sequence. In such a situation asymmetrical division will help reduce costs and increase efficiency through the use of reagents that have been previously generated.

In the methods of the invention the smaller polynucleotide sequences common to all the individual polynucleotide sequences in each individual branch group are identified if the branch group contains more than one individual polynucleotide sequence. This step would not be performed for a branch group that contains only one individual polynucleotide sequence.

In the methods of the invention the smaller polynucleotide sequences common to all the individual polynucleotide sequences in a first branch group are compared to the smaller polynucleotide sequences from all other branch groups. Such comparison can be accomplished by, for example, pairwise sequence alignment using alignment algorithms or other comparison techniques well known in the art.

In the methods of the invention the smaller polynucleotide sequences common to all branch groups are identified.

In the methods of the invention the smaller polynucleotide sequences common to only a subset of branch groups are identified.

In the methods of the invention the smaller polynucleotide sequences unique to each individual polynucleotide sequence in each branch group are identified. A "unique" smaller polynucleotide sequence is not identical to any of the smaller polynucleotide sequences that the other individual polynucleotide sequences in a collection have been divided into. If a smaller polynucleotide sequence is "unique" it cannot also be common to a "subset of branch groups."

In the methods of the invention the smaller polynucleotide sequences identified in the preceding three steps of the method and that are required to synthesize a larger individual polynucleotide in the collection are provided. These smaller polynucleotides may be common to all branch groups, common to a subset of branch groups, or unique to an individual polynucleotide sequence. In this step of the invention the smaller polynucleotide sequences are physically provided. Additionally, the smaller polynucleotides sequences may be provided manually or by the use of a computer controlled robot.

The smaller polynucleotides provided can be single stranded DNAs or RNAs that are unmodified and have 5' phosphate groups and 3' hydroxyl groups. Alternatively, such smaller polynucleotides may have been modified chemically or enzymatically to facilitate a given joining method to be subsequently performed during the synthesis of a given individual polynucleotide sequence. Such polynucleotides may also contain nucleobases that are promiscuous and can pair with an array of other different nucleobases or tolerate mismatched base pairings. Structurally these smaller polynucleotides should be equivalent to the smaller polynucleotide sequences that each individual polynucleotide in the sequence was divided into. This means that the polynucleotide sequence is identical to a given smaller polynucleotide sequence, or can hybridize to a sequence that is complementary to the smaller polynucleotide. Those skilled in the art will readily recognize appropriate chemical or enzymatic modifications for facilitating the joining of smaller polynucleotide sequences and structurally equivalent polynucleotides that may be provided in the methods of the invention. Importantly, the smaller polynucleotides sequences may be provided manually or by the use of a computer controlled robot.

In the methods of the invention an individual polynucleotide sequence in the collection is synthesized. Such synthesis can be performed manually or by the use a computer-controlled robot. A computer directed, automated DNA synthesizer is one example of such a machine. Such a DNA synthesizer and related methods are described in published US Patent Application No. 20070054277 A1 entitled "Computer-directed Assembly of a Polynucleotide Encoding a Target Polypeptide," the entire disclosure of which is herein incorporated by reference.

Synthesis of a given single-stranded polynucleotide chain can be accomplished by standard methods for joining nucleotides such as those methods utilizing phosphoramidite chemistry, polynucleotide ligation (e.g. ligase chain reaction), or other appropriate methods which are well known in the art. Joining can be accomplished using polynucleotides conjugated to an insoluble material, or in a mobile phase as appropriate for a given synthesis method. Double-stranded polynucleotide chains can be made by synthesizing the complementary strand of a given single-stranded polynucleotide chain and annealing the two single-stranded polynucleotide to create a double-stranded polynucleotide such as a DNA. Alternatively, polymerase chain reaction based methods may be used, with appropriate primers, to make a double-stranded polynucleotide from a single-stranded polynucleotide molecule. Double-stranded polynucleotide synthesis techniques utilizing staggered, complementary, single-stranded polynucleotides may also be used in the methods of the invention to generate double-stranded polynucleotide molecules.

Those skilled in the art will recognize other well known techniques that may also be used in the methods of the invention to generate a double-stranded polynucleotide. Exemplary synthesis methods are disclosed in issued U.S. Pat. No. 6,521,427 entitled "Method for the Complete Chemical Synthesis and Assembly of Genes and Genomes," the entire disclosure of which is herein incorporated by reference.

In the methods of the invention the preceding two steps are performed until each individual polynucleotide sequence in the collection of partially identical polynucleotides is synthesized. The synthesis of each individual polynucleotide sequence in a collection can be performed sequentially or be performed in parallel. Similarly, the other steps of the methods of the invention may be performed sequentially, or in parallel as appropriate.

In one embodiment of the method of the invention the smaller polynucleotide sequences are from 2 to 96 nucleotide residues in length.

In another embodiment of the method of the invention the smaller polynucleotide sequences are 48 nucleotide residues in length. Such a polynucleotide of 48 nucleotide residues in length will contain 16 triplet codons.

In another embodiment of the method of the invention the individual polynucleotide sequence is a double-stranded polynucleotide sequence. Such a double-stranded polynucleotide sequence may be a DNA, RNA, or comprise both DNA and RNA.

The methods of the invention permit a collection of unique, partially identical individual polynucleotide sequences to be synthesized using a minimal number of polynucleotide synthesis reagents. The advantages of this method are a decrease in the size of the reagent pool, a decrease in the amount of smaller premade polynucleotide reagents required, and a decrease in the amount of time needed to synthesize a collection of unique, partially identical individual polynucleotide sequences relative to other methods. The methods here may also be fully automated by the use of computers and computer controlled robots.

The present invention is further described with reference to the following examples. These examples are merely to illustrate aspects of the present invention and are not intended as limitations of this invention.

EXAMPLE 1

The methods of the invention can be performed as follows. First, a collection of unique, partially identical individual polynucleotide sequences to be synthesized were identified. In the present example a collection of three partially identical polynucleotide sequences derived from human TLR3 were selected. These partially identical polynucleotide sequences were designated "Collection Polynucleotide 1" (SEQ ID NO: 1), "Collection Polynucleotide 2" (SEQ ID NO: 2), and "Collection Polynucleotide 3" (SEQ ID NO: 3) as shown in the CLUSTALW alignment in FIG. 2. FIG. 2 is a multiple sequence alignment generated using the default settings of the CLUSTALW algorithm used by the Mega3.1 Molecular Evolutionary Genetics Analysis Program (see Kumar et al., supra). The collection of polynucleotides to be synthesized (FIG. 2) were partially identical relative to each other having different nucleotide residues at only position 74, position 113 and position 128.

Second, the collection of partially identical polynucleotide sequences were analyzed with a phylogeny tree algorithm to make a phylogenetic tree. The Mega3.1 program was used to generate a phylogenetic tree that included each individual polynucleotide (e.g. SEQ ID NO: 1, SEQ ID NO: 2, and SEQ ID NO: 3) in the collection of unique, partially identical polynucleotides to be synthesized. Evolutionary distances between each individual polynucleotide sequence were determined by comparing the sequences nucleotide-by-nucleotide using the Neighbor-Joining method and the default settings for this method in the Mega3.1 program. These settings include the use of the Kimura 2-Parameter Model for calculating evolutionary distances.

Figure 3:
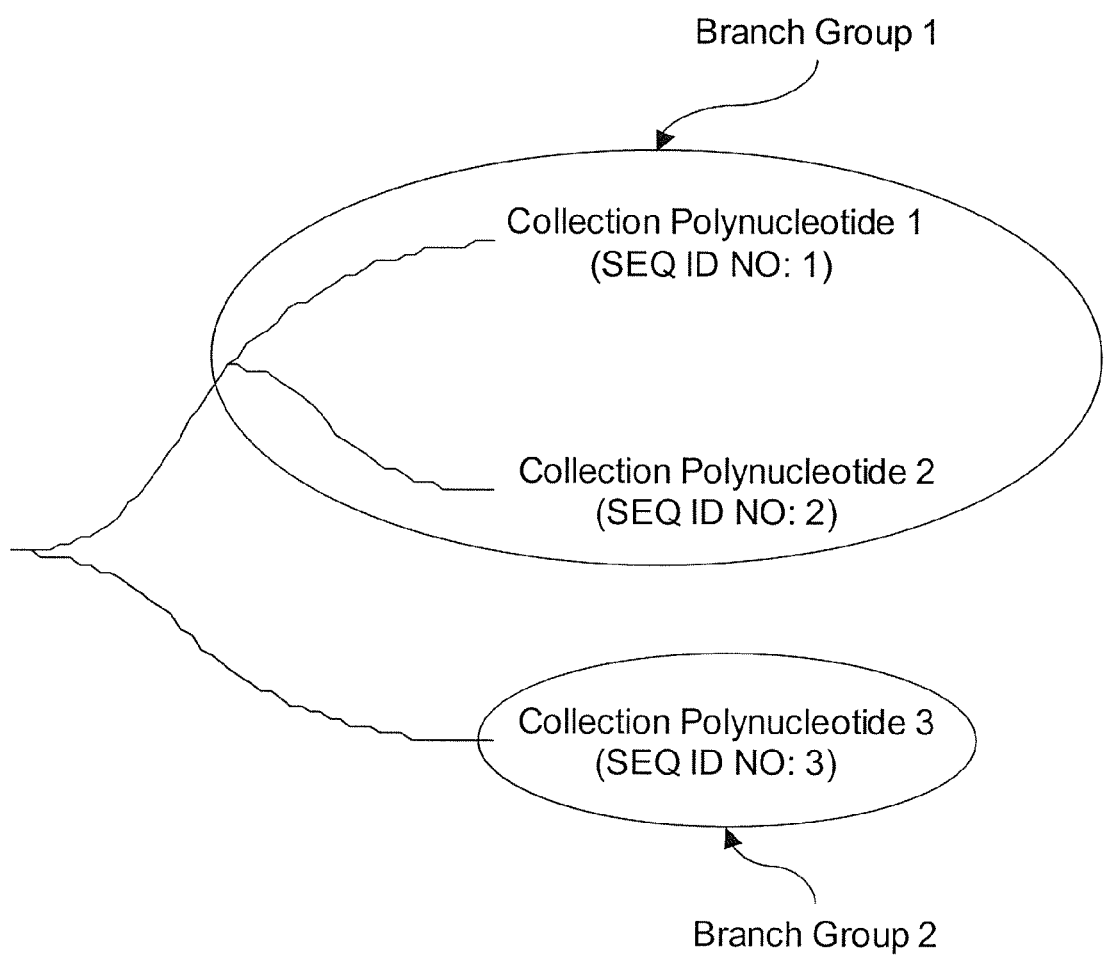
FIG. 3 shows a phylogenetic tree describing the relatedness of Collection Polynucleotide 1 (SEQ ID NO: 1), Collection Polynucleotide 2 (SEQ ID NO: 2), and Collection Polynucleotide 3 (SEQ ID NO: 3) relative to each other. Branch Group 1 and Branch Group 2 are also identified on the tree.

A rooted phylogenetic tree that graphically represents the evolutionary distances between sequences was then generated using the Tree Explorer module of Mega3.1 (FIG. 3).

In FIG. 3, the evolutionary distance between SEQ ID NO: 1 and SEQ ID NO: 3 is represented by the distance of the line from SEQ ID NO: 1 through the root of this tree and then to SEQ ID NO: 3. This distance is large and reflects the more extensive substitutions between these sequences. The evolutionary distance between SEQ ID NO: 1 and SEQ ID NO: 2 is represented by the distance of the line from SEQ ID NO: 1 through the nearest branch point and then to SEQ ID NO: 2. This distance is small and reflects the less extensive substitutions between these sequences.

Third, each individual branch group of the phylogenetic tree was identified by examining the phylogenetic tree to spot the nodes on the tree, such as a root or branch point, and then determining which polynucleotide sequences are connected to a given node on the tree by shorter evolutionary distances relative to other more distant sequences.

In FIG. 3, two identified branch groups are shown. The first group is designated "Branch Group 1" and is connected to a branch point on the tree. The second group is designated "Branch Group 2" and is connected to the root of the tree.

Fourth, each individual polynucleotide sequence in each individual branch group was identified. Branch Group 1, for example, contains contains two individual polynucleotide sequences, SEQ ID NO: 1 and SEQ ID NO: 2, comprising 144 nucleotides which are closely related based on the small evolutionary distances between them. Branch Group 2, in contrast, contains one individual polynucleotide sequence, SEQ ID NO: 3, comprising 144 nucleotides.

Figure 4:
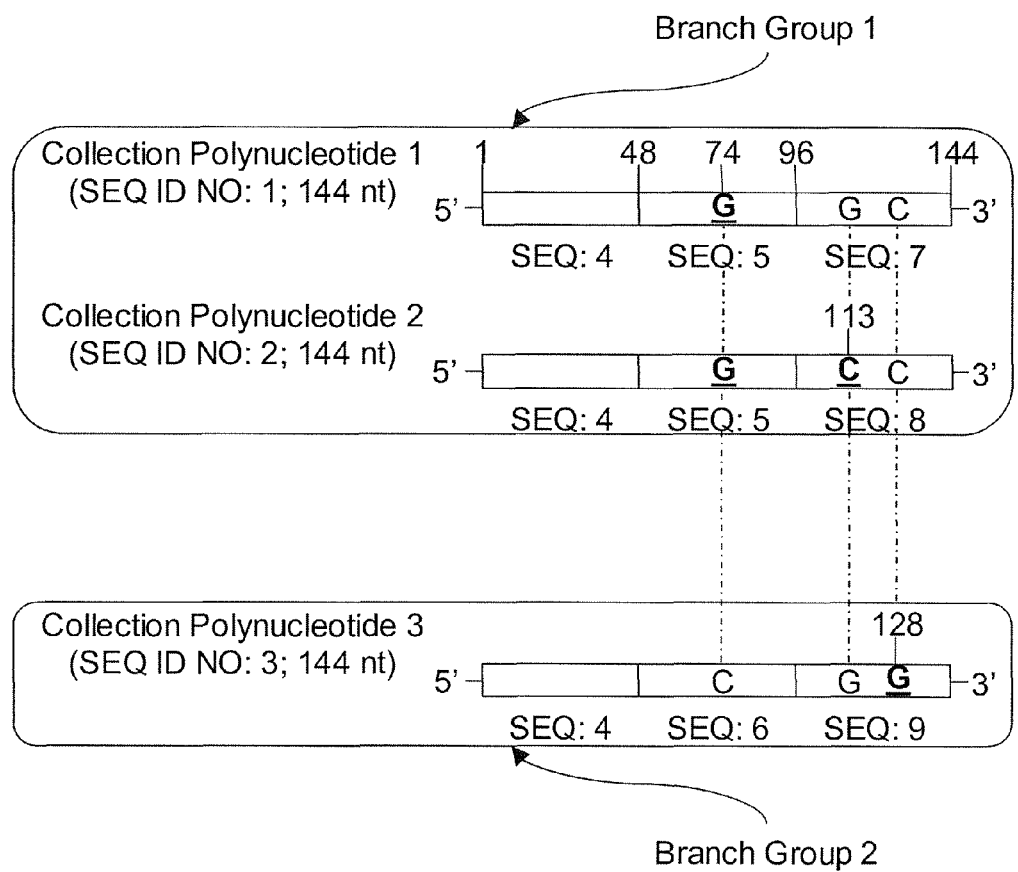
FIG. 4 shows the division of the larger individual polynucleotides in Branch Group 1 and Branch Group 2 of the collection into smaller polynucleotide sequences of 48 nucleotides each. Mutations relative to the wild-type Homo sapiens TLR3 sequence at each varied position are shown in bold and underlined.

Fifth, each individual polynucleotide sequence in each branch group was divided into smaller polynucleotide sequences (FIG. 4). For example, the larger individual polynucleotide sequence designated SEQ ID NO: 1 from branch group 1 is divided into three smaller polynucleotide sequences of 48 nucleotides each which are designated SEQ ID NO: 4, SEQ ID NO: 5, and SEQ ID NO: 7. SEQ ID NO: 2 from branch group 1 is also divided into three smaller polynucleotide sequences of 48 nucleotides each. These sequences are designated as SEQ ID NO: 4, SEQ ID NO: 5, and SEQ ID NO: 8. SEQ ID NO: 3 from branch group 2 is also divided into three smaller polynucleotide sequences of 48 nucleotides each. These sequences are designated as SEQ ID NO: 4, SEQ ID NO: 6, and SEQ ID NO: 9.

Sixth, the smaller polynucleotide sequences common to all the individual polynucleotide sequences in each individual branch group was identified. This step is performed when a branch group contains more than one individual polynucleotide sequence; it was not performed for branch group 2 that contains only one individual polynucleotide sequence. A comparison of the smaller polynucleotide sequences from branch group 1 reveals that the smaller polynucleotide sequences designated SEQ ID NO: 4 and SEQ ID NO: 5 are shared by both the larger individual polynucleotide sequences (designated SEQ ID NO: 1 and SEQ ID NO: 2) in branch group 1. In other words, the smaller polynucleotide sequences designated SEQ ID NO: 4 and SEQ ID NO: 5 are common to all of the individual polynucleotide sequences (SEQ ID NO: 1 and SEQ ID NO: 2) in branch group 1.

Seventh, the smaller polynucleotide sequences common to all the individual polynucleotide sequences in a first branch group were compared with the smaller polynucleotide sequences from all other branch groups. In this example, the smaller polynucleotide sequences SEQ ID NO: 4 and SEQ ID NO: 5 are common to each of the individual polynucleotides sequences in branch group 1. These sequences, SEQ ID NO: 4 and SEQ ID NO: 5, were compared to the smaller polynucleotides sequences designated SEQ ID NO: 4, SEQ ID NO: 6, and SEQ ID NO: 9 that the larger individual polynucleotide designated SEQ ID NO: 3 in branch group 2 (the only other branch group in this example) has been previously divided into (FIG. 4).

Figure 5:
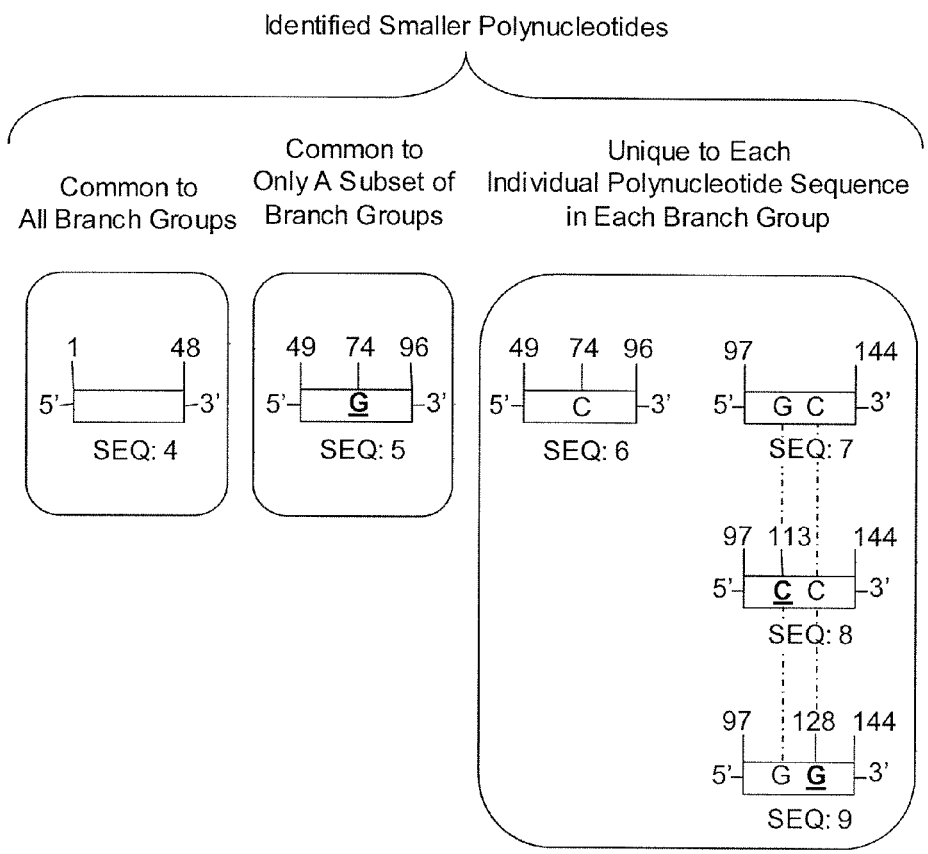
FIG. 5 shows the identification of smaller polynucleotide sequences common to all branch groups, common only to a subset of branch groups, and unique to each individual polynucleotide sequence in each branch group. Mutations relative to the wild-type Homo sapiens TLR3 sequence at each varied position are shown in bold and underlined.

Eighth, the smaller polynucleotide sequences common to all branch groups were identified (FIG. 4 and FIG. 5). In this example, SEQ ID NO: 4 and SEQ ID NO: 5 from branch group 1 were compared to SEQ ID NO: 4, SEQ ID NO: 6, and SEQ ID NO: 9 from branch group two. After this comparison, the smaller polynucleotide sequences common to all branch groups were identified, namely SEQ ID NO: 4 (FIGS. 4 and 5).

Ninth, the smaller polynucleotide sequences common to only a subset of branch groups were identified (FIGS. 4 and 5). SEQ ID NO: 1 and SEQ ID NO: 2 in branch group 1 were divided into three smaller polynucleotide sequences of 48 nucleotides each. SEQ ID NO: 5 is one of these smaller polynucleotide sequences and is common to both SEQ ID NO: 1 and SEQ ID NO: 2, but is not found in any other branch group. Consequently, SEQ ID NO: 5 is common only to a subset of branch groups. Here, that subset is branch group 1, but in other more complex collections of individual polynucleotides the subset may include more than one branch group, but such a subset could not include all branch groups identified on a phylogenetic tree for such a collection.

Tenth, the smaller polynucleotide sequences unique to each individual polynucleotide sequence in each branch group were identified (FIG. 4 and FIG. 5). The smaller polynucleotide sequence shown in SEQ ID NO: 7 is unique to the larger individual polynucleotide designated SEQ ID NO: 1 which is in branch group 1. The smaller polynucleotide sequence SEQ ID NO: 8 is unique to the larger individual polynucleotide designated SEQ ID NO: 2 which is also in branch group 1. The smaller polynucleotide sequences SEQ ID NO: 6 and SEQ ID NO: 9 are both unique to the larger individual polynucleotide designated SEQ ID NO: 3 which is in branch group 2.

Figure 6:
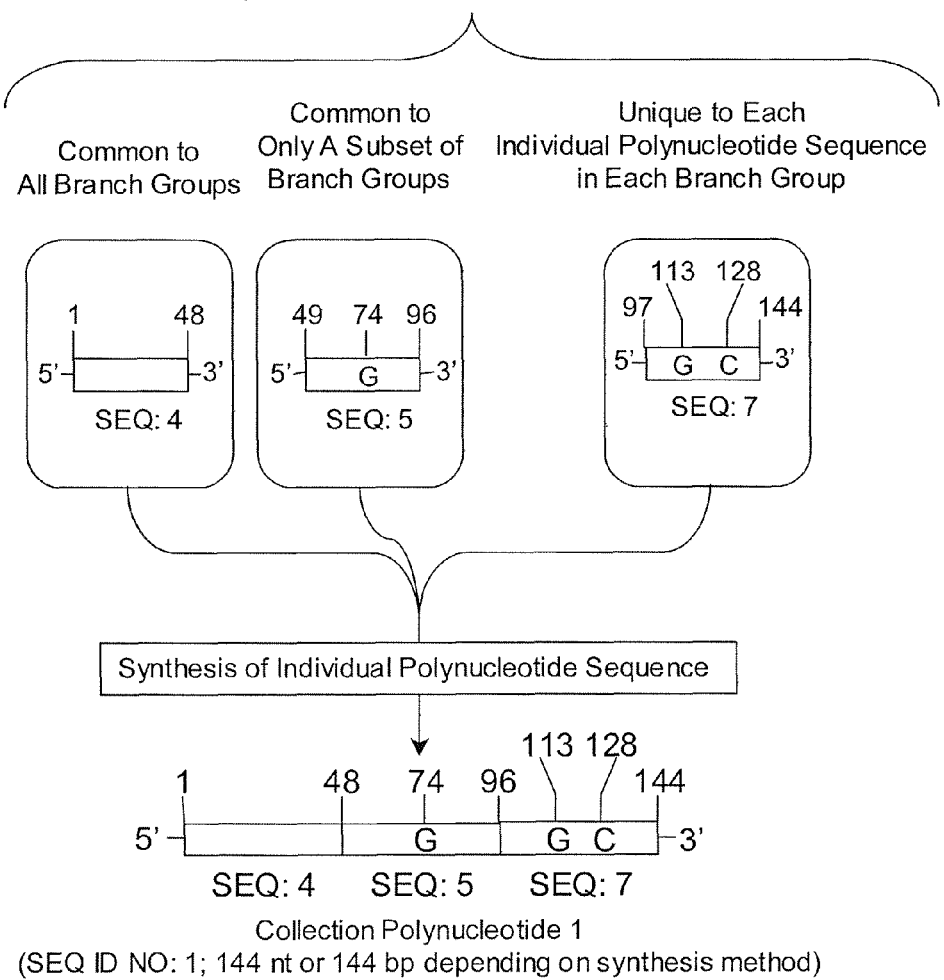
FIG. 6 shows the provision of the smaller polynucleotide sequences required to synthesize Collection Polynucleotide 1 (SEQ ID NO: 1) from Branch Group 1 and the product of this synthesis. Mutations relative to the wild-type Homo sapiens TLR3 sequence at each varied position are shown in bold and underlined.

Eleventh, the smaller polynucleotide sequences identified in the preceding three steps that are required to synthesize a larger individual polynucleotide sequence in the collection can be provided. For example, to synthesize a single stranded polynucleotide corresponding to SEQ ID NO: 1 from branch group 1 three smaller polynucleotide sequences must be physically provided (FIG. 6). These sequences are SEQ ID NO: 4 which is common to all branch groups, SEQ ID NO: 5 which is common only to branch group 1, and SEQ ID NO: 7 which is unique to the larger individual polynucleotide sequence designated SEQ ID NO: 1 in branch group 1.

Twelfth, an individual polynucleotide sequence can be synthesized. The larger individual polynucleotide sequence designated SEQ ID NO: 1 in branch group 1 can be synthesized from the smaller polynucleotides SEQ ID NO: 4, SEQ ID NO: 5 and SEQ ID NO: 7.

Thirteenth, the preceding two steps will be performed until each individual polynucleotide sequence in the collection of partially identical polynucleotides is synthesized. The individual polynucleotide sequence designated SEQ ID NO: 2 from branch group 1 can be synthesized when the smaller polynucleotides designated SEQ ID NO: 4, SEQ ID NO: 5 and SEQ ID NO: 8 are physically provided and then joined. SEQ ID NO: 4 is common to all branch groups, SEQ ID NO: 5 is common only to branch group 1, and SEQ ID NO: 8 is unique to the larger individual polynucleotide sequence designated SEQ ID NO: 2 in branch group 1.

The individual polynucleotide sequence designated SEQ ID NO: 3 from branch group 2 can be synthesized when the smaller polynucleotides designated SEQ ID NO: 4, SEQ ID NO: 6 and SEQ ID NO: 9 are provided and then joined. SEQ ID NO: 4 is common to all branch groups, while SEQ ID NO: 6 and SEQ ID NO: 9 are both unique to the larger individual polynucleotide sequence designated SEQ ID NO: 3 in branch group 2. None of the smaller polynucleotides that SEQ ID NO: 3 was divided into are shared across a subset of the branch groups identified. Stated differently, none of the smaller polynucleotide sequences that SEQ ID NO: 3 was divided into are common to only a subset of branch groups.

The present invention now being fully described, it will be apparent to one of ordinary skill in the art that many changes and modifications can be made thereto without departing from the spirit or scope of the appended claims.

The invention claimed is:

1. A method for synthesizing a collection of partially identical polynucleotides, comprising:
   a) identifying a collection of unique, partially identical individual polynucleotide sequences to be synthesized;
   b) analyzing the polynucleotide sequences with a phylogeny tree algorithm to make a phylogenetic tree;
   c) identifying each individual branch group of the phylogenetic tree;
   d) identifying each individual polynucleotide sequence in each individual branch group identified;
   e) dividing each individual polynucleotide sequence in each branch group into smaller polynucleotide sequences;
   f) identifying the smaller polynucleotide sequences common to all the individual polynucleotide sequences in each individual branch group identified if the branch group contains more than one individual polynucleotide sequence;
   g) comparing the smaller polynucleotide sequences common to all the individual polynucleotide sequences in a first branch group with the smaller polynucleotide sequences from all other branch groups;
   h) identifying the smaller polynucleotide sequences common to all branch groups;
   i) identifying the smaller polynucleotide sequences common to only a subset of branch groups;
   j) identifying the smaller polynucleotide sequences unique to each individual polynucleotide sequence in each branch group;

k) providing the smaller polynucleotide sequences of step h), step i), or step j) required to synthesize an individual polynucleotide sequence in a branch group;
l) synthesizing the individual partially identical polynucleotide sequence; and
m) repeating steps k) and l) until each individual polynucleotide sequence in the collection of partially identical polynucleotides is synthesized.

2. The method of claim 1 wherein the smaller polynucleotide sequences are from 2 to 96 nucleotide residues in length.

3. The method of claim 1 wherein the smaller polynucleotide sequences are 48 nucleotide residues in length.

4. The method of claim 1 wherein the individual polynucleotide sequence is a double-stranded polynucleotide sequence.

\* \* \* \* \*